(12) United States Patent
Bendek et al.

(10) Patent No.: US 7,169,132 B2
(45) Date of Patent: Jan. 30, 2007

(54) MEDICATION DELIVERY PEN

(75) Inventors: Antonio Bendek, Vernon, NJ (US); Lucio Giambattista, East Hanover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 281 days.

(21) Appl. No.: 10/676,341

(22) Filed: Oct. 1, 2003

(65) Prior Publication Data
US 2004/0127858 A1 Jul. 1, 2004

Related U.S. Application Data

(60) Provisional application No. 60/415,198, filed on Oct. 1, 2002.

(51) Int. Cl.
*A61M 5/00* (2006.01)

(52) U.S. Cl. ...................... 604/208; 604/187

(58) Field of Classification Search ............... 604/132, 604/134, 136, 138, 156, 181, 187, 218, 71, 604/207–208, 211, 224, 252
See application file for complete search history.

(56) References Cited

U.S. PATENT DOCUMENTS 5,320,609 A * 6/1994 Haber et al. ............... 604/135
5,591,136 A * 1/1997 Gabriel ...................... 604/211
5,725,508 A * 3/1998 Chanoch et al. ........... 604/207
6,221,046 B1   4/2001 Burroughs et al.
6,221,053 B1 * 4/2001 Walters et al. ............. 604/211

FOREIGN PATENT DOCUMENTS

EP          0 937 476 A2    8/1999
EP            937476 A2 *   8/1999

* cited by examiner

*Primary Examiner*—Nicholas D Lucchesi
*Assistant Examiner*—Christopher D. Koharski
(74) *Attorney, Agent, or Firm*—David M. Fortunato; Hoffmann & Baron, LLP

(57) ABSTRACT

A medication delivery pen is provided having a lead screw with an enlarged portion at a first end thereof and an end longitudinally opposite the first end in contacting engagement with a plunger of a medication cartridge. The lead screw is selectively axially displaceable by a user when selectively administering a predetermined dosage amount of medication for injection into a patient. The medication delivery pen also includes a driver coaxially disposed about the lead screw; and, a reset ring non-rotatably disposed on the driver and axially slidable thereon and therealong. The reset ring is axially movable with respect to the driver when a dosage amount is set by a user of the medication delivery pen. The reset ring engages the enlarged portion of the lead screw upon a predetermined extent of relative axial movement between the reset ring and the lead screw. With this arrangement, the reset ring advantageously prevents setting a dose on a medication delivery pen that is greater than the medication which is available.

29 Claims, 8 Drawing Sheets

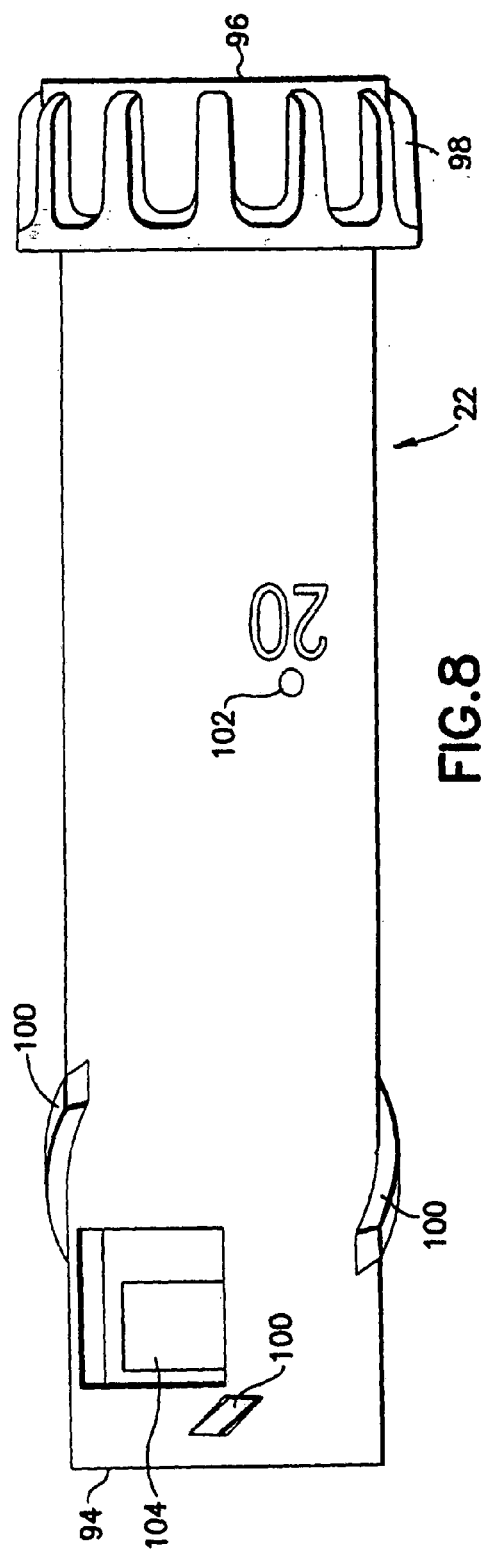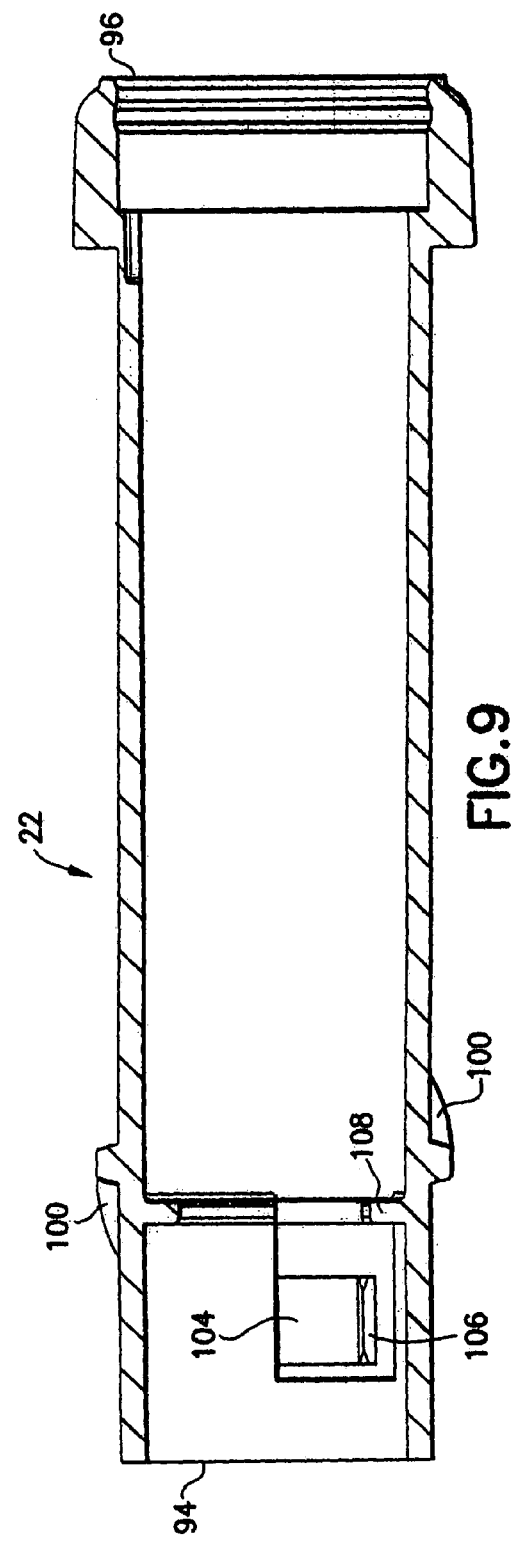

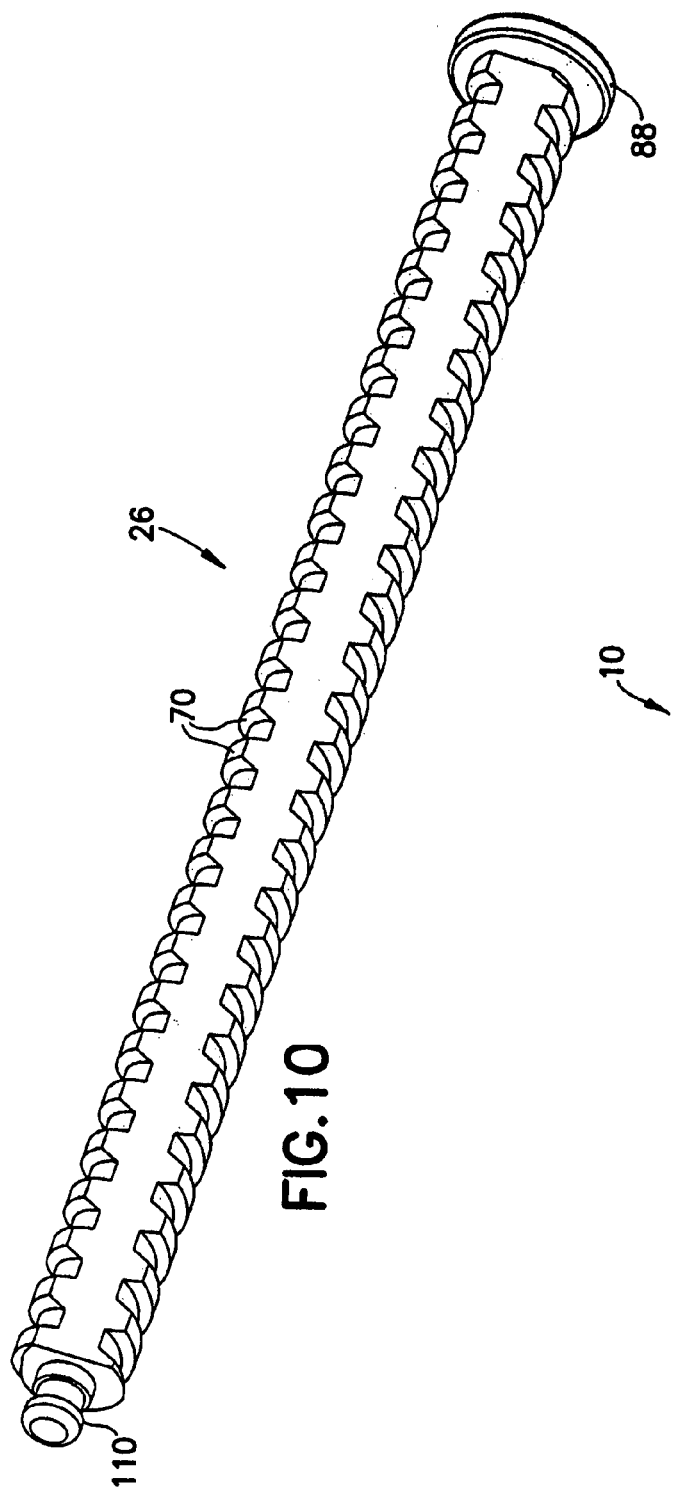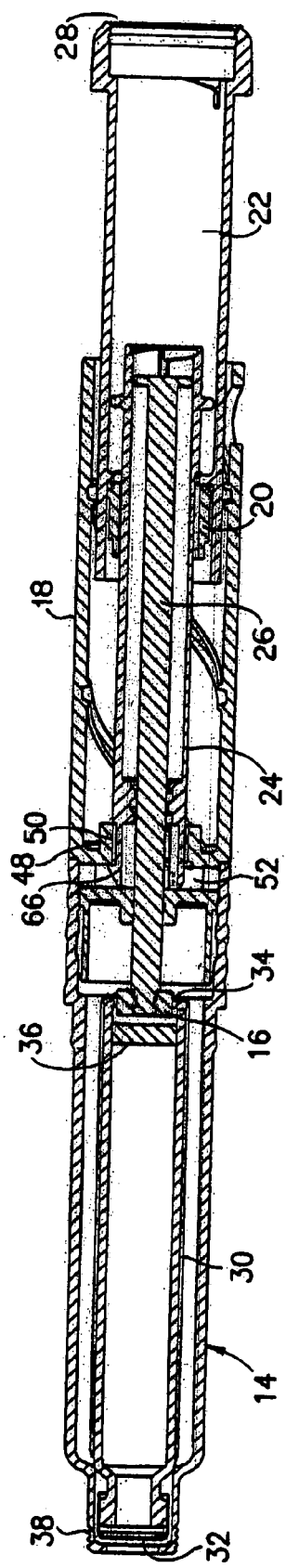

MEDICATION DELIVERY PEN

CROSS-REFERENCE TO PRIOR APPLICATIONS

This application claims priority of U.S. Provisional Patent Application No. 60/415,198, filed Oct. 1, 2002.

FIELD OF THE INVENTION

The present invention relates to fixed and adjustable dose medication delivery pens.

BACKGROUND OF THE INVENTION

Hypodermic syringes are used to deliver selected doses of medication to patients. The prior art hypodermic syringe typically includes a syringe barrel having opposed proximal and distal ends; the proximal end being generally defined as the end located away from a patient, and the distal end being generally defined as the end located near the patient during use. A cylindrical chamber wall extends between the proximal and distal ends and defines a fluid containing chamber. The proximal end of the prior art syringe barrel is substantially open and receives a plunger in sliding fluid tight engagement with an interior surface of the chamber wall. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in direction toward the proximal end (a proximal direction) draws fluid through the lumen of the needle cannula and into the chamber. Movement of the plunger in a direction toward the distal end (a distal direction) urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction after the needle has been caused to pierce the patient's skin or by injection into an intravenous tube or other similar device or structure.

Some medication, such as insulin, is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for selecting a dose of medication to be delivered by the pen and a driving apparatus for urging the plunger of the vial in a distal direction for a distance corresponding to the selected dose.

The user of the prior art pen mounts a double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to a zero setting upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body, and removes and discards the empty vial. A new vial can be inserted into the vial holder, and the vial holder and pen body can be reassembled and used as explained above.

The above described medication delivery pen is effective and much more convenient for self-administration of medication than the hypodermic syringes that use separate medication vials. However, prior art medication delivery pens have their shortcomings. For example, prior art medication delivery pens do not prevent the patient from dialing a dose that is greater than the amount of medication remaining in the vial. For example, a patient may thus dial a dose of 0.45 ml, when only 0.30 ml of medication remains in the vial. The patient would only discover that fact after the medication was delivered, and the dose set knob was prevented from complete displacement by the set screw abutting the bottom of the vial. The patient would then have to determine the unadministered amount and use another vial to complete delivery of the desired dose. Such a situation would require two injections be made for administration of a single dose. That obvious inconvenience and additional discomfort from a second injection, in addition to the replacement of the spent vial, render such prior art self-administration devices unsatisfactory.

There is thus a need in the art for a medication delivery pen that overcomes the above-described shortcomings of the prior art.

SUMMARY OF THE INVENTION

To overcome the shortcomings of the prior art, a medication delivery pen is provided having a lead screw with an enlarged portion at a first end thereof and an end longitudinally opposite the first end in contacting engagement with a plunger of a medication cartridge. The lead screw is selectively axially displaceable by a user when selectively administering a predetermined dosage amount of medication for injection into a patient. The medication delivery pen also includes a driver coaxially disposed about the lead screw; and, a reset ring non-rotatably disposed on the driver and axially slidable thereon and therealong. The reset ring is axially movable with respect to the driver when a dosage amount is set by a user of the medication delivery pen. The reset ring engages the enlarged portion of the lead screw upon a predetermined extent of relative axial movement between the reset ring and the lead screw. With this arrangement, the reset ring advantageously prevents setting a dose on a medication delivery pen that is greater than the medication which is available.

These and other features of the invention will be better understood through a study of the following detailed description and accompanying drawings.

BRIEF DESCRIPTION OF THE DRAWINGS

FIGS. 8 and 9 are plan and cross-sectional views, respectively, of a dose knob of a medication delivery pen constructed in accordance with the subject invention;

FIG. 10 is a perspective view of a lead screw of a medication delivery pen constructed in accordance with the subject invention;

FIG. 11 is a cross-sectional view of an assembled medication delivery pen constructed in accordance with the subject invention;

DETAILED DESCRIPTION OF THE INVENTION

Figure 1:
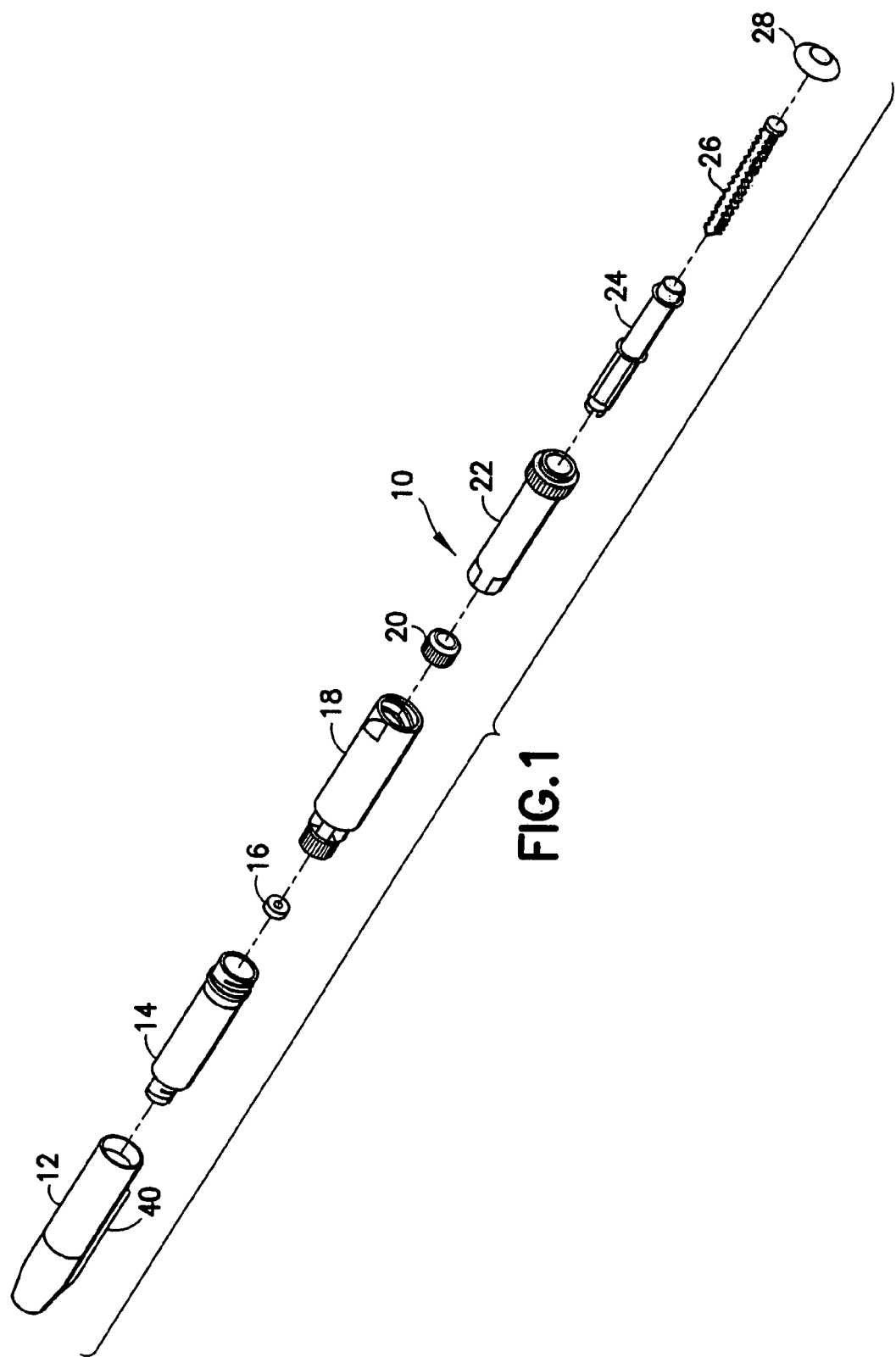
FIG. 1 is an exploded view of a medication delivery pen constructed in accordance with the subject invention.

With reference to the Figures, particularly FIG. 1, a medication delivery pen is shown and generally designated with the reference numeral 10. The medication delivery pen 10 may be used for the administration of various medications, including insulin; unless specified otherwise, the medication does not comprise a part of the present invention. In addition, the term "medication" is used in an illustrative and non-limiting manner to refer to any substance that may be injected into a patient for any purpose. The medication delivery pen 10 of the present invention may also be reusable or disposable.

The subject invention relates to limiting dose-setting at near-completion or completion of a drug cartridge as described below. As will be recognized by those skilled in the art and from the disclosure provided herein, various medication pen delivery designs can be used consistent with the teachings herein. To illustrate the subject invention, a representative, preferred embodiment of a medication delivery pen is described. Other embodiments and designs are within the scope and spirit of the subject invention.

With reference to FIG. 1, the medication delivery pen 10 generally includes a cap 12, a cartridge holder 14, a spinner 16, a body 18, a reset ring 20, a dose knob 22, a driver 24, a lead screw 26, and a thumb button 28. With reference to FIG. 11, the cartridge holder 14 is formed to accommodate a drug cartridge 30, which may be of any conventional design. By way of non-limiting example, the drug cartridge 30 may include an elastomeric septum 32 at a proximal end thereof and an open distal end 34 which exposes a slidable plunger 36. Drug medication is contained within the drug cartridge 30 between the septum 32 and the plunger 36. As will be described in more detail below, the spinner 16 is configured to engage the plunger 36 and force forward movement thereof in expelling drug from the drug cartridge 30. A needle (not shown) is required to administer drug from the medication delivery pen 10. The needle may be a double-ended cannula which is threadedly mounted onto threads 38 of the cartridge holder 14. One end of the cannula is exposed for insertion into a patient, while the second end of the cannula is disposed to pierce the septum 32 of the drug cartridge 30. After administration of the dose, the needle is removed, with the septum 32 self-sealing. The cap 12 is formed to releasably mount onto the cartridge holder 14, such as with a snap fit, to limit contamination of the septum 32 and the surrounding portions of the cartridge holder 14. A resilient holding arm 40 may extend from the cap 12 to provide holding force for the pen 10 in a patient's pocket. One or more windows (not shown) may also be provided in the cartridge holder 14 to give a visual indication of the drug level in the drug cartridge 30.

Figure 2:
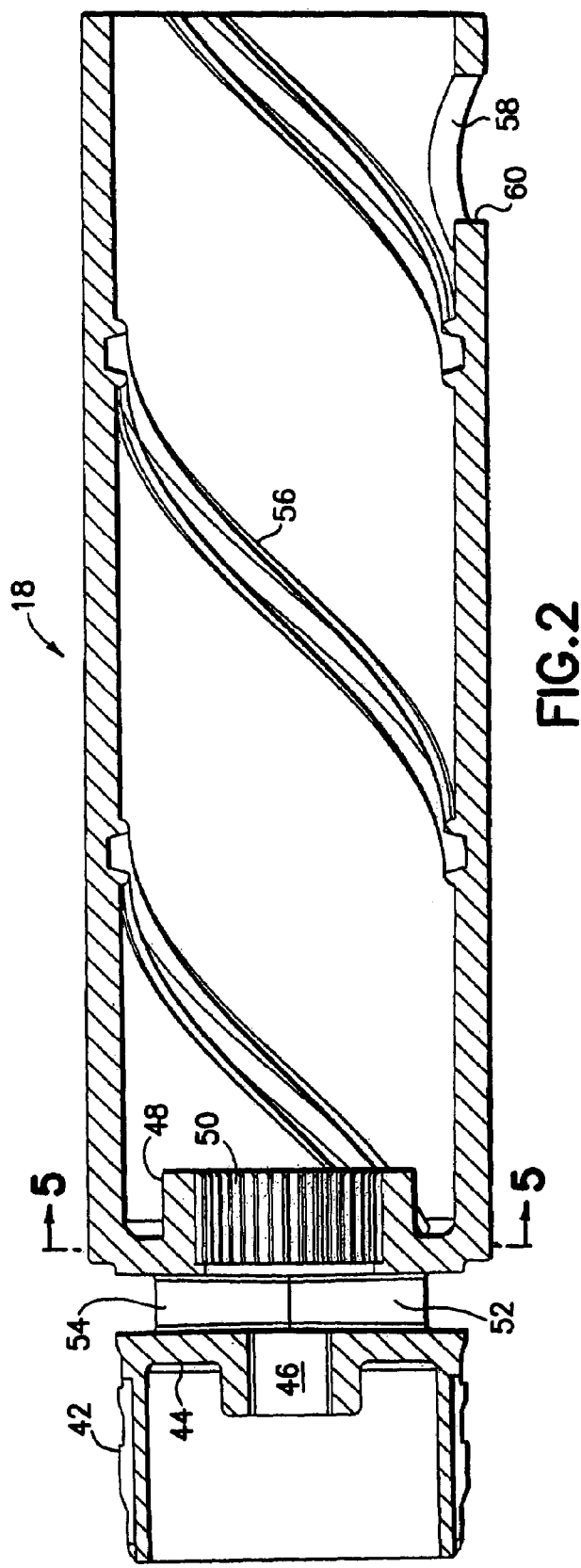
FIG. 2 is a cross-sectional view of a body of a medication delivery pen constructed in accordance with the subject invention.

With reference to FIG. 2, the body 18 is generally cylindrical, and may have threads or detents 42 which releasably engage (for a reusable embodiment) the cartridge holder 14. A bulkhead 44 extends across the interior of the body 18 through which an aperture 46 is formed. The aperture 46 is defined to allow the non-rotational passage of the lead screw 26 therethrough. The body 18 also includes an interiorly-supported cylindrical wall 48 which defines a channel 50 therethrough. A transverse recess 52 is defined between the aperture 46 and the channel 50 which is at least partially bounded by wall 54, that may be continuous or discontinuous. In addition, a dose setting thread 56 is formed on the interior of the body 18, along with a window 58 for dosage selection. A pointer 60 may be defined on the body 18 that extends into the window 58 to clearly point out a selected dosage level.

Figure 3:
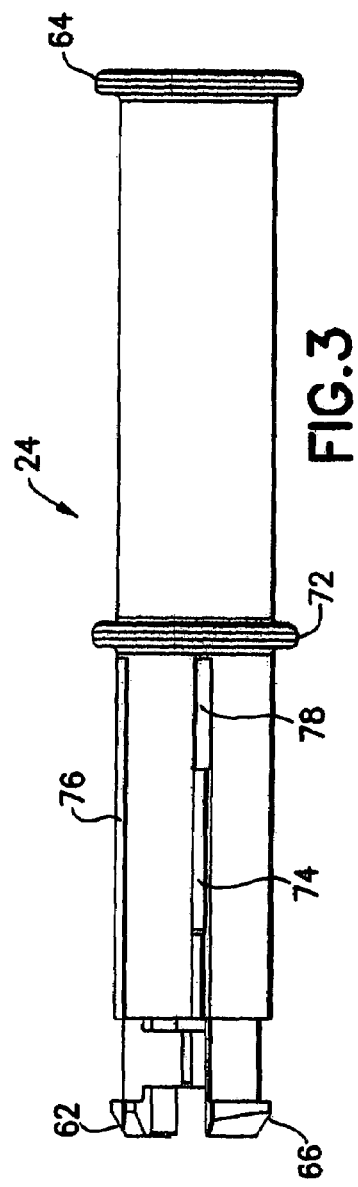
FIGS. 3 and 4 are plan and cross-sectional views, respectively, of a driver of a medication delivery pen constructed in accordance with the subject invention.
Figure 4:
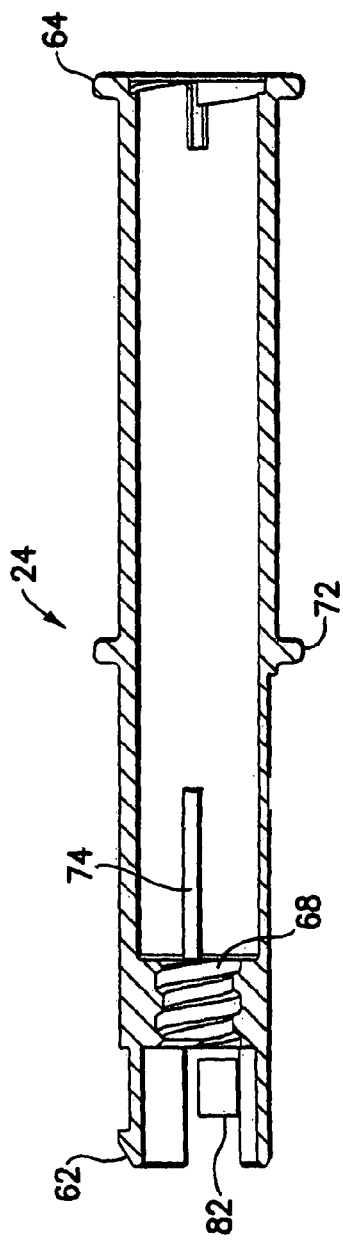
Figure 6:
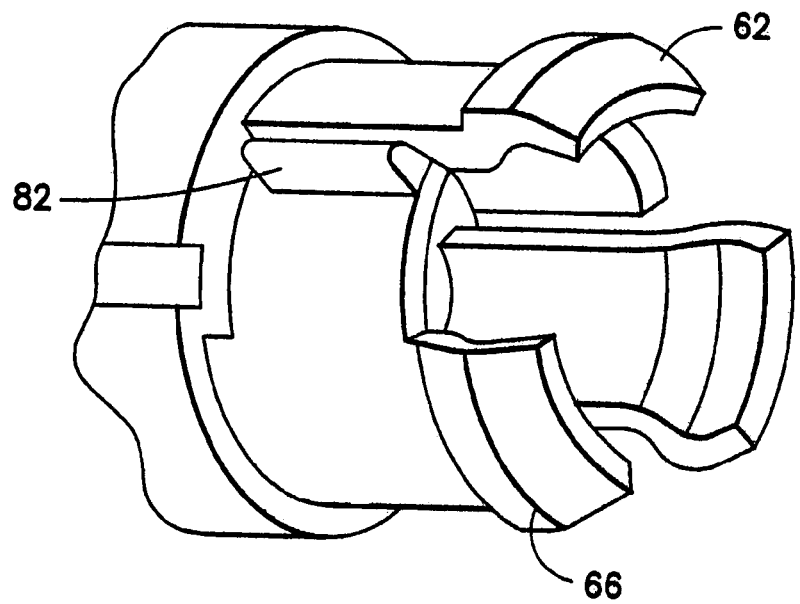
FIG. 6 is a perspective view of the proximal end of the driver of FIG. 3.

With reference to FIGS. 3, 4 and 6, the driver 24 includes proximal and distal ends 62 and 64, respectively, with a snap ring 66 being formed at the proximal end 62. The snap ring 66 is formed to pass through the channel 50 of the body 18 and lock onto the wall 48 in the recess 52 (FIG. 11). With the snap ring connection, the driver 24 is fixed axially relative to the body 18, yet is able to rotate relative thereto. Internal threads 68 are also provided to threadedly engage threads 70 of the lead screw 26 (FIG. 10). Additionally, as best shown in FIGS. 3 and 4, an annular stop 72 is preferably provided midway along the length of the driver 24.

One or more longitudinal keyways 74 are defined on the driver 24 that extend completely through the wall thereof. One or more limited-depth channels 76 may also be formed on the driver 24, and limited-depth slots 78 preferably extend longitudinally from the keyways 74 towards the distal end 64. The limited-depth channels 76 and the limited-depth slots 78 do not extend fully through the wall of the driver 24. Preferably, two of the keyways 74 are provided and located diametrically apart. It is also preferred that the limited-depth channels 76 and the limited-depth slots 78 generally terminate at the annular stop 72.

Figure 5:
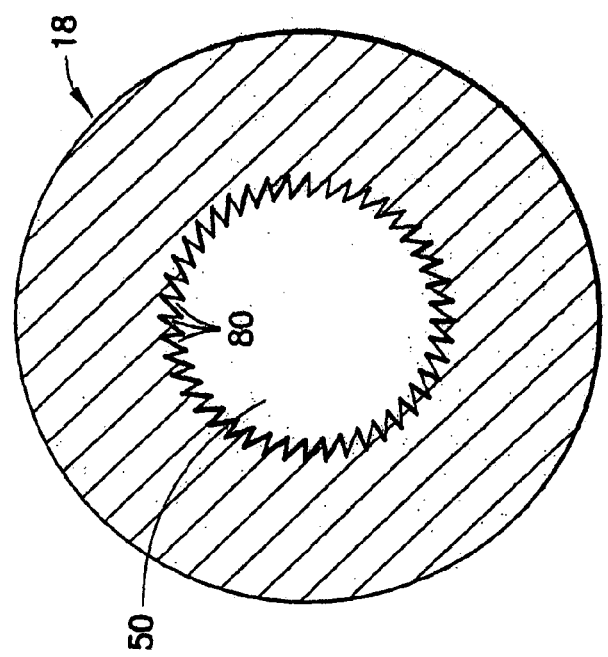
FIG. 5 is a cross-sectional view taken along line 5—5 of FIG. 2.

In a preferred construction of the body 18, as shown in FIG. 5, a plurality of ratchet teeth 80 extend from the cylindrical wall 48. In addition, and as best shown in FIG. 6, one or more ratchet fingers 82 are formed on the proximal end 62 of the driver 24 and are located in proximity to the snap ring 66. The ratchet fingers 82 are positioned within the channel 50 when the driver 24 is locked in the recess 52 (FIG. 11). Preferably, the ratchet teeth 80 and the ratchet fingers 82 are formed to cooperate to allow the driver 24 to rotate in only one direction relative to the body 18. Consequently, the ratchet teeth 80 and the ratchet fingers 82 provide a measure of protection against unwanted rearward movement of the lead screw 26 resulting from the driver 24 inadvertently rotating in a reverse direction.

Figure 7:
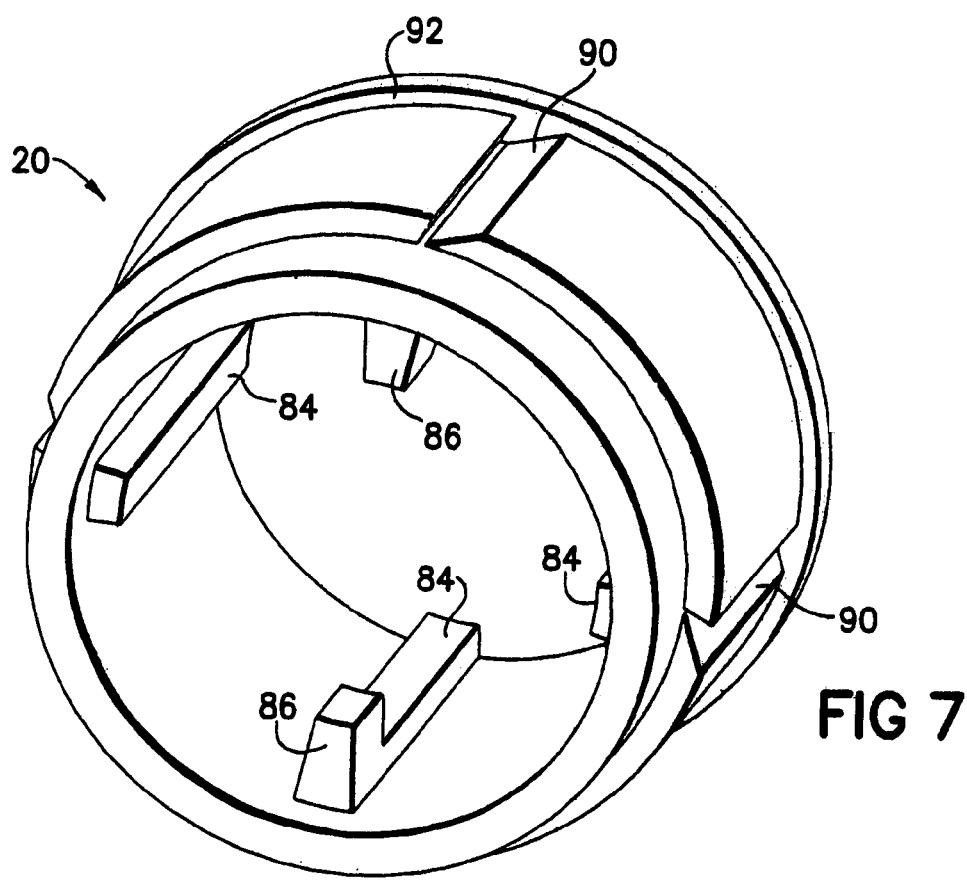
FIG. 7 is a perspective view of a reset ring of a medication delivery pen constructed in accordance with the subject invention.

With reference to FIG. 7, the reset ring 20 is tubular with, preferably, one or more inwardly extending splines 84 which are formed and located to be disposed in the limited-depth channels 76 and, if provided, the limited-depth slots 78 of the driver 24. With the splines 84 extending into the limited-depth channels 76 and the limited-depth slots 78, the reset ring 20 cannot be rotated relative to the driver 24. However, the splines 84 are formed such to allow the reset ring 20 to axially move along the length of the limited-depth channels 76 and the limited-depth slots 78. Also, as shown in FIG. 7, one or more protrusions 86 extend inwardly in the reset ring 20 which are formed and positioned to extend through the keyways 74 with the reset ring 20 being disposed on the driver 24. The protrusions 86 must have sufficient length to engage an enlarged portion 88 formed on the lead screw 26 (FIG. 10). It is preferred that more than one of the protrusions 86 be provided and at spaced-apart locations so that the enlarged portion 88 may be firmly engaged. In a preferred arrangement, the protrusions 86 extend from and are formed unitarily with the splines 84. Alternatively, as will be recognized by those skilled in the art, the protrusions 86 may be formed separately from the splines 84. Also, the splines 84 need not be provided; here, the protrusions 86 and the keyways 74 together can act to prevent relative rotation between the reset ring 20 and the driver 24, yet allow for the reset ring 20 to axially slide along the driver 24. Also, with this arrangement, the limited-depth channels 76 and the limited-depth slots 78 need not be provided.

In addition, grooves 90 are formed about the periphery of the reset ring 20, preferably at equal intervals, and an annular rim 92 preferably extends radially beyond the grooves 90 at one end of the reset ring 20.

As shown in FIGS. 8 and 9, the dose knob 22 is generally tubular having open proximal and distal ends 94 and 96, respectively. A textured handle 98 is formed in proximity to the distal end 96 which is engagable by a user to rotate the dose knob 22 in setting a desired dosage amount on the pen 10. The dose knob 22 includes one or more thread portions 100 externally formed to threadedly engage the dose setting thread 56 of the body 18. Accordingly, the dose knob 22 may be rotated within the body 18 resulting in translation of that rotation to axial displacement of the dose knob 22 relative to the body 18 in setting a desired dose. Dosage indicia 102 may also be disposed externally of the dose knob 22.

The dose knob 22 preferably includes one or more ratchet arms 104 formed to be biased inwardly. With reference to FIG. 11, in a fully-assembled state of the pen 10, the dose knob 22 is coaxially disposed about the reset ring 20 with the ratchet arms 104 being aligned with the grooves 90 of the reset ring 20 so that rotation of the dose knob 22 relative to the reset ring 20 results in the ratchet arms 104 acting against the reset ring 20 in a ratcheting manner giving a user an audible signal of such rotation. Preferably, each of the ratchet arms 104 is formed with an inwardly extending detent 106 at an end thereof. It is preferred that the grooves 90 and the detents 106 coact to only permit rotation of the dose knob 22 relative to the reset ring 20 in one rotational direction. An inwardly extending lip 108 may optionally be provided in longitudinally aligning the reset ring 20 relative to the ratchet arms 104.

With reference to FIG. 10, the lead screw 26 may be of any conventional type and is formed with a connecting end 110 onto which the spinner 16 is mountable using any known technique. With reference once again to FIG. 1, the thumb button 28 is also of any known conventional design and, as will be appreciated by those skilled in the art, may be mounted to the distal end 96 of the dose knob 22 using any technique.

With reference to FIG. 11, the completed assembly of the pen 10 is shown in cross-section. In operation, the dose knob 22 is dialed to a desired dose as indicated by the dosage indicia 102 which is viewable through the window 58 of the body 18. As the dose knob 22 is rotated, the ratchet arms 104 rotate about the reset ring 90 and engage the grooves 90. The ratchet arms 104 also engage the annular rim 92 of the reset ring 20 and urge the reset ring 20 axially and distally, without the reset ring 20 rotating, in concert with the distal movement of the dose knob 22. Once set at a desired dose, the ratchet arms 104 are urged to engage the next encountered grooves 90. The resiliency of the ratchet arms 104 provide a holding force that maintains the dose knob 22 in a fixed longitudinal position relative to other components of the pen 10. Thereafter, the thumb button 28 is engaged and forced proximally resulting in rearward rotation of the dose knob 22 relative to the body 18 with the reset ring 20 and the dose knob 22 being driven in a proximal direction. Because of the fixed interengagement between the ratchet arms 104 and the grooves 90, and the thread portions 100 of the dose knob 22 rotating within the dose setting thread 56 of the body 18, the reset ring 20 rotates together with the dose knob 22. In turn, the driver 24 is forced to rotate with the reset ring 20 due to the non-rotatable connection therebetween. The internal threads 68 of the driver 24 thus rotate about the lead screw 26, and because the lead screw 26 cannot rotate within the aperture 46, the lead screw 26 is caused to be translated proximally without rotation. As the lead screw 26 moves proximally, the spinner 16 engages the slidable plunger 36 and forces proximal movement thereof resulting in the expulsion of a desired dosage. Once the dose has been administered, this process can be repeated.

Figure 12:
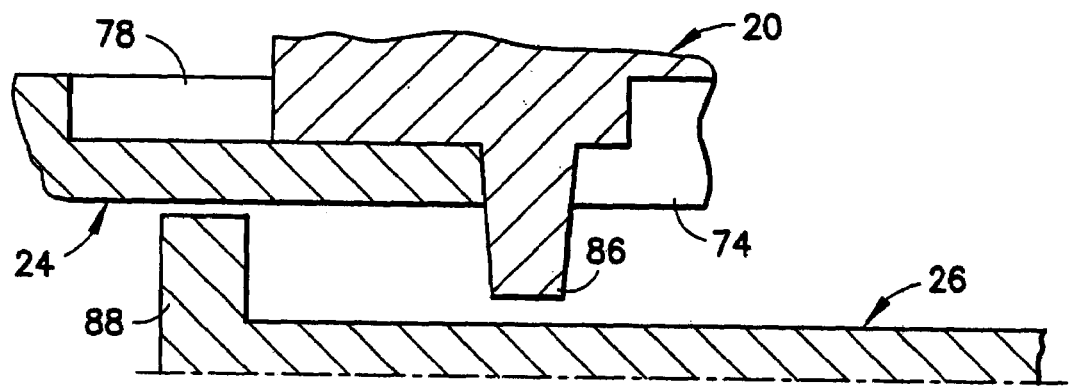
FIGS. 12 and 13 schematically depict the manner in which protrusions formed on the reset ring limit movement relative to the lead screw.
Figure 13:
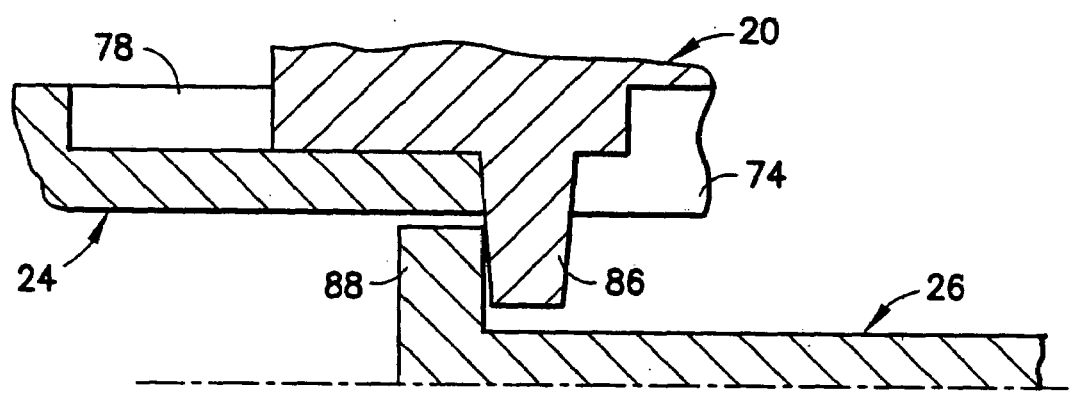

With the subject invention, the protrusions 86 advantageously prevent the dose knob 22 from being set to a dose greater than which is available for administration. With reference to FIG. 12, the enlarged portion 88 of the lead screw 26 is spaced from the protrusions 86 during normal operation and any desired dosage can be achieved. As shown in FIG. 13, with the drug cartridge 30 nearing completion, the setting of the dose knob 22 to a greater setting than available medication will result in the protrusions 86 engaging the enlarged portion 88 of the lead screw and not allowing the reset ring 20 to be axially moved therebeyond in a distal direction. As a result, the protrusions 86 establish the maximum amount that may be administered at that time, which may be less than a desired amount. As is readily apparent to those skilled in the art, the keyways 74, the protrusions 86, the enlarged portion 88 and other components are appropriately formed and positioned to preferably coincide the engagement of the protrusions 86 with the enlarged portion 88 to the amount of available medication for dosing.

Figure 14:
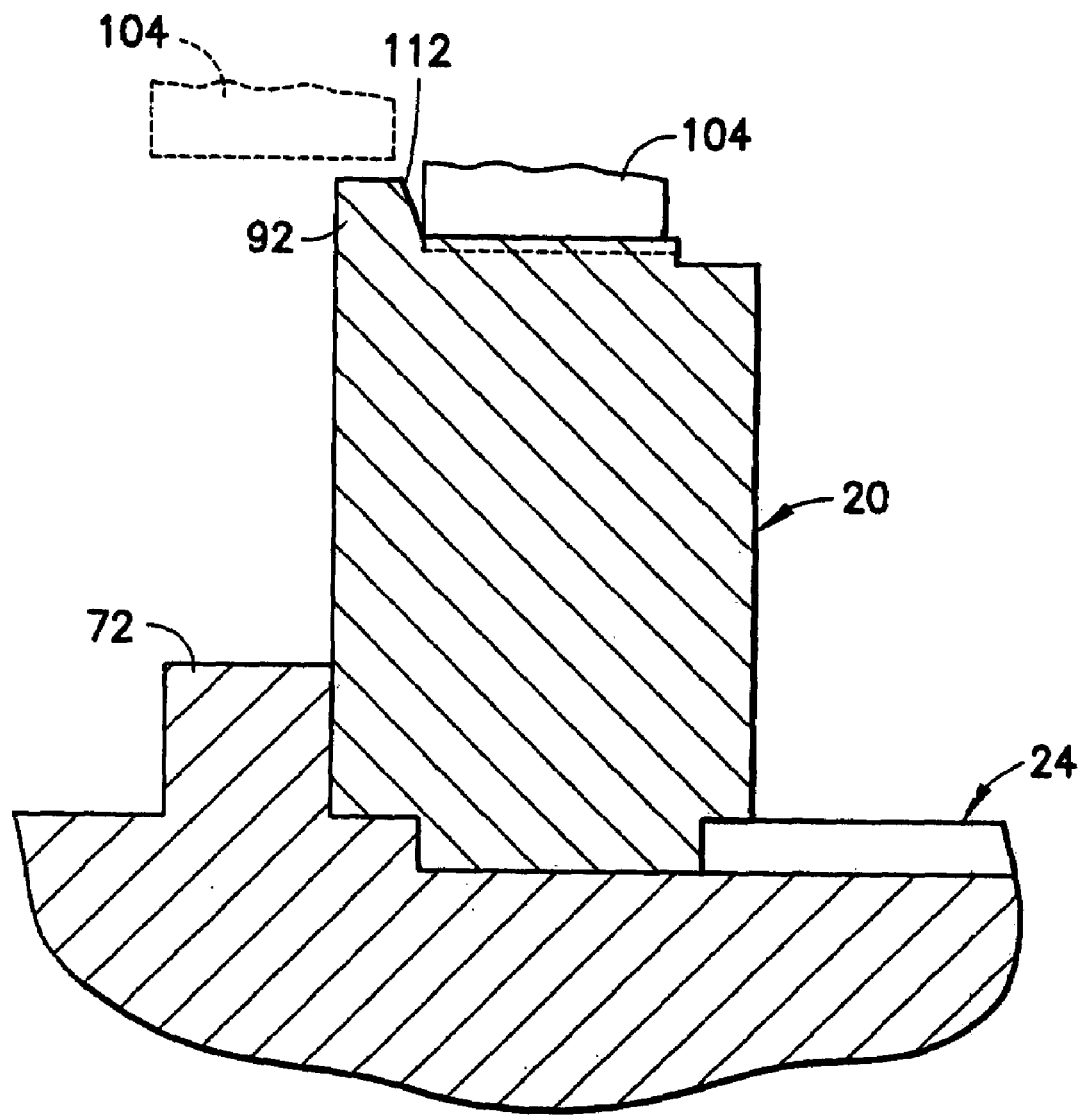
FIG. 14 schematically depicts a resettable configuration of the reset ring of the subject invention.

As will be appreciated by those skilled in the art, the subject invention may be used with resettable and non-resettable designs. For example, as shown in FIG. 14, the annular rim 92 of the reset ring 20 may be formed with a proximally-facing ramped surface 112. Thus, with the reset ring 20 being urged fully distally and into engagement with the annular stop 72 on the driver 24, further dialing of the dose knob 22 causes the ramped surface 112 to go under the ratchet arms 104 thereby disengaging the reset ring 20 from the dose knob 22. The reset ring 20 can be reengaged by the dose knob 22 at its most proximal position relative to the driver 24 coinciding with a zero dosage amount. With the annular rim 92 being formed flat instead of ramped, such resettability can be generally avoided.

In addition, the pen 10 may be a fixed dose design or a variable dose design as described above. With a fixed dose design, the annular stop 72 can be positioned so that the dose knob 22 is dialed to a predetermined amount with the reset ring 20 engaging the annular stop 72. For variable dose designs, the annular stop 72 can be positioned to define a maximum dose amount allowing a user a wide dosage range. With the pen 10 being resettable and variable-dosing, a mistake in dosage setting can be corrected by fully dialing out the dose knob 22 and causing the pen 10 to be reset to zero.

The pen 10 may be formed as a disposable single use pen where the drug cartridge 30 cannot be replaced once spent. Here, the cartridge holder 14 is preferably permanently (i.e., non-removably) coupled to the body 18. Alternatively, the pen 10 can be of the multiple use variety with the drug cartridge 30 being replaceable; preferably, with this arrangement, the cartridge holder 14 is removably mountable to the body 18.

While the invention has been described in relation to the preferred embodiments with several examples, it will be understood by those skilled in the art that various changes may be made without deviating from the spirit and scope of the invention as defined in the appended claims.

What is claimed is:

1. A medication delivery pen having a cartridge containing a predetermined amount of medication for injection into a patient, the cartridge having a plunger axially movable therein to expel the medication from the cartridge, said medication delivery pen comprising:
   a lead screw having an enlarged portion at a first end thereof, said lead screw having an end longitudinally opposite said first end in contacting engagement with the plunger, said lead screw being selectively axially displaceable by a user when selectively administering a predetermined dosage amount of medication for injection into a patient;
   a driver coaxially disposed about said lead screw; and
   a reset ring non-rotatably disposed on said driver and axially slidable thereon and therealong, said reset ring being axially movable with respect to said driver and said lead screw when a dosage amount is set by a user of said medication delivery pen, wherein said reset ring includes at least one protrusion which engages said enlarged portion of said lead screw upon a predetermined extent of relative axial movement between said reset ring and said lead screw.

2. A medication delivery pen as in claim 1, wherein said reset ring includes at least one protruding spline.

3. A medication delivery pen as in claim 2, wherein said driver includes a keyway and a limited-depth channel spaced from said keyway, and wherein said protrusion is formed to extend through said keyway, said spline being formed to extend into, and axially slide along, said channel.

4. A medication delivery pen as in claim 2, wherein said driver includes a limited-depth slot extending longitudinally from said keyway, said spline being formed to extend into, and axially slide along, said slot.

5. A medication delivery pen as in claim 2, wherein said protrusion and said spline are unitarily formed.

6. A medication delivery pen as in claim 1, wherein said driver includes an annular stop disposed midway along the length thereof.

7. A medication delivery pen as in claim 1, wherein said reset ring includes an annular rim.

8. A medication delivery pen as in claim 7, wherein at least one surface of said annular rim being ramped.

9. A medication delivery pen as in claim 1, wherein said dosage amount is less than the predetermined amount of medication in the cartridge, and wherein multiple dosages may be administered using a single cartridge.

10. A device for setting and administering a dose of medication for a medication delivery pen having a cartridge containing a predetermined amount of medication for injection into a patient, the cartridge having a plunger axially movable therein to expel the medication from the cartridge, said device comprising:
    a body;
    a lead screw contained within said body and having an enlarged portion at a distal end thereof, said lead screw having a proximal end in contacting engagement with the plunger, said lead screw being selectively axially displaceable in a distal to proximal direction by a user of the medication delivery pen when selectively administering a predetermined dosage amount of medication for injection into a patient;
    a driver coaxially disposed about said lead screw and provided within said body; and
    a reset ring non-rotatably disposed on said driver and axially slidable thereon and therealong, said reset ring being axially movable with respect to said driver and said lead screw when a dosage amount is set by the user, wherein said reset ring includes at least one protrusion which engages said enlarged portion of said lead screw upon a predetermined extent of relative axial movement between said reset ring and said lead screw to limit the dosage amount to no more than the amount of medication contained in the cartridge.

11. A device as in claim 10, further comprising a dose knob provided in said body, said dose knob being selectively rotatable with respect to the body by the user to set the dosage amount, and being axially displaceable with respect to said body by the user to expel the dosage amount of medication from the cartridge, rotation of said dose knob by the user causing axial proximal to distal displacement of said dose knob and said reset ring, axial displacement of said dose knob by the user causing distal to proximal distal to proximal movement of said lead screw and expulsion of the dosage amount.

12. A device as in claim 10, wherein said reset ring includes at least one protruding spline.

13. A device as in claim 12, wherein said driver includes a keyway and a limited-depth channel spaced from said keyway, and wherein said protrusion is formed to extend through said keyway, said spline being formed to extend into, and axially slide along, said channel.

14. A device as in claim 12, wherein said driver includes a limited-depth slot extending longitudinally from said keyway, said spline being formed to extend into, and axially slide along, said slot.

15. A device as in claim 12, wherein said protrusion and said spline are unitarily formed.

16. A device as in claim 10, wherein said driver includes an annular stop disposed midway along the length thereof.

17. A device as in claim 10, wherein said reset ring includes an annular rim.

18. A device as in claim 17, wherein at least one surface of said annular rim being ramped.

19. A device as in claim 10, wherein said dosage amount is less than the predetermined amount of medication in the cartridge, and wherein multiple dosages may be administered using a single cartridge.

20. A medication delivery pen for delivering a dosage amount of medication from a cartridge containing a predetermined amount of medication for injection into a patient, the cartridge having a plunger axially movable therein to expel the medication from the cartridge, said medication delivery pen comprising:

a cartridge holder within which the cartridge may be held;

a body coupled to said cartridge holder;

a lead screw contained within said body and having an enlarged portion at a distal end thereof, said lead screw having a proximal end in contacting engagement with the plunger, said lead screw being selectively axially displaceable in a distal to proximal direction by a user of the medication delivery pen when selectively administering a predetermined dosage amount of medication for injection into a patient;

a driver coaxially disposed about said lead screw and provided within said body;

a reset ring non-rotatably disposed on said driver and axially slidable thereon and therealong, said reset ring being axially movable with respect to said driver and said lead screw when a dosage amount is set by the user, wherein said reset ring includes at least one protrusion which engages said enlarged portion of said lead screw upon a predetermined extent of relative axial movement between said reset ring and said lead screw to limit the dosage amount to no more than the amount of medication contained in the cartridge; and a dose knob provided in said body, said dose knob being selectively rotatable with respect to the body by the user to set the dosage amount, and being axially displaceable with respect to said body by the user to expel the dosage amount of medication from the cartridge, rotation of said dose knob by the user causing axial proximal to distal displacement of said dose knob and said reset ring, axial displacement of said dose knob by the user causing distal to proximal distal to proximal movement of said lead screw and expulsion of the dosage amount.

21. A medication delivery pen as in claim 20, wherein said cartridge holder and said body are non-removably coupled together, said medication delivery pen further comprising a cartridge.

22. A medication delivery pen as in claim 20, wherein said reset ring includes at least one protruding spline.

23. A medication delivery pen as in claim 22, wherein said driver includes a keyway and a limited-depth channel spaced from said keyway, and wherein said protrusion is formed to extend through said keyway, said spline being formed to extend into, and axially slide along, said channel.

24. A medication delivery pen as in claim 22, wherein said driver includes a limited-depth slot extending longitudinally from said keyway, said spline being formed to extend into, and axially slide along, said slot.

25. A medication delivery pen as in claim 22, wherein said protrusion and said spline are unitarily formed.

26. A medication delivery pen as in claim 20, wherein said driver includes an annular stop disposed midway along the length thereof.

27. A medication delivery pen as in claim 20, wherein said reset ring includes an annular rim.

28. A medication delivery pen as in claim 27, wherein at least one surface of said annular rim being ramped.

29. A medication delivery pen as in claim 20, wherein said dosage amount is less than the predetermined amount of medication in the cartridge, and wherein multiple dosages may be administered using a single cartridge.

* * * * *